United States Patent
She et al.

(10) Patent No.: US 11,879,101 B2
(45) Date of Patent: Jan. 23, 2024

(54) BREVIBACILLUS AGRI, PREPARATION THEREOF, METHOD FOR PREPARING SURFACTANT AND USE THEREOF

(71) Applicant: Yangtze University, Wuhan (CN)

(72) Inventors: Yuehui She, Wuhan (CN); Fan Zhang, Wuhan (CN); Zhi Zhang, Wuhan (CN); Puyong Yao, Wuhan (CN); Fei Li, Wuhan (CN); Hao Dong, Wuhan (CN); Shanshan Sun, Wuhan (CN); Gaoming Yu, Wuhan (CN); Shaojin Yi, Wuhan (CN); Wenda Zhang, Wuhan (CN); Linqi Hu, Wuhan (CN); Yangyang Feng, Wuhan (CN); Anying Zheng, Wuhan (CN); Yang Li, Wuhan (CN)

(73) Assignee: Yangtze University, Wuhan (CN)

( * ) Notice: Subject to any disclaimer, the term of this patent is extended or adjusted under 35 U.S.C. 154(b) by 212 days.

(21) Appl. No.: 17/317,812

(22) Filed: May 11, 2021

(65) Prior Publication Data
US 2022/0049165 A1   Feb. 17, 2022

(30) Foreign Application Priority Data
Aug. 13, 2020 (CN) .......................... 202010813094.X

(51) Int. Cl.
- *C12N 1/20* (2006.01)
- *C10G 32/00* (2006.01)
- *C12P 21/00* (2006.01)
- *C12P 21/02* (2006.01)
- *C12R 1/01* (2006.01)

(52) U.S. Cl.
CPC ............. *C10G 32/00* (2013.01); *C12N 1/205* (2021.05); *C12R 2001/01* (2021.05)

(58) Field of Classification Search
None
See application file for complete search history.

(56) References Cited

FOREIGN PATENT DOCUMENTS

CN    1132933 C    12/2003

OTHER PUBLICATIONS

She et al., "Genome sequence of *Brevibacillus agri* strain 5-2, isolated from the formation water of petroleum reservoir", Marine Genomics 18:123-125, 2014 (Year: 2014).*
She et al., "Investigation of Indigenous Microbial Enhanced Oil Recovery in a Middle Salinity Petroleum Reservoir", Advanced Materials Research 365:326-331, 2011 (Year: 2011).*

* cited by examiner

*Primary Examiner* — David Steadman
(74) *Attorney, Agent, or Firm* — The Dobrusin Law Firm, P.C.

(57) ABSTRACT

The present disclosure relates to the technical field of application of bioengineering technology in microbial oil recovery, and discloses a *Brevibacillus agri* strain and preparation thereof and a method for preparing surfactant, and use thereof. The *Brevibacillus agri* strain is deposited in the China General Microbiological Culture Collection Center under the accession number CGMCC No. 9983. The *Brevibacillus agri* and its preparation may effectively enhance the crude oil recovery; the method for preparing the surfactant allow the lipopeptide biosurfactant to have good physical properties, effectively reduce the surface tension, and have good emulsifying performance for petroleum, various hydrocarbons and lipids.

10 Claims, 6 Drawing Sheets

BREVIBACILLUS AGRI, PREPARATION THEREOF, METHOD FOR PREPARING SURFACTANT AND USE THEREOF

CROSS REFERENCE TO RELATED APPLICATION

This application claims the priority of Chinese Patent Application No. 202010813094.X, entitled "*Brevibacillus agri*, preparation thereof and method for preparing surfactant and use thereof" filed with the China National Intellectual Property Administration on Aug. 13, 2020, which is incorporated herein by reference in its entirety.

TECHNICAL FIELD

The disclosure relates to the application of bioengineering technology in the field of microbial enhanced oil recovery, and in particular to a *Brevibacillus agri* strain and preparation thereof, and to a method for preparing surfactant and use of the surfactant.

BACKGROUND ART

Microbial enhanced oil recovery (MEOR) is considered as the replacement technology for tertiary oil recovery (i.e. the quaternary recovery) due to its simple operation, economy, environmental protection and sustainable development characteristics. In early 2017, microbial enhanced oil recovery was rated as one of the top ten world petroleum technology advances by PetroChina in 2016, which is becoming more and more widely used in China's oilfields, from the oilfields of eastern China, for example Daqing, Shengli, Dagang, Huabei and Jilin, to the oilfields of western China, for example Xinjiang, Qinghai, Changqing and Tuha. In particular, in recent years, the microbial enhanced oil recovery has been successfully applied in low permeability reservoirs and heavy oil reservoirs. The indigenous microorganisms of the oil reservoir can metabolize different substrates, and produce biosurfactants, biopolysaccharides, biogas, bioacids, biosolvents, etc., and synergistically enhance oil recovery. The viscosity reduction of crude oil through dispersion and emulsification by the produced biosurfactant is an important mechanism of MEOR.

For example, the Chinese patent with application number CN 01115920.0 discloses Bacillus brevis and its use in removing sulfur from the sulfur-containing organic compounds. The *Bacillus brevis* involved in the disclosure is *Bacillus brevis* R-6 strain which was deposited in "China General Microbiological Culture Collection Center" on Apr. 29, 2001 under the accession number of CGMCC NO. 0571. R-6 strain was isolated from aerobic activated sludge in oily wastewater treatment pool of a refinery, from oil contaminated soil around oil wells and from soil samples around coal mines with high sulfur content. The *Bacillus brevis* R-6 strain and its non-growth stationary cell liquid, immobilized cell, cell liquid culture or crude enzyme extract can remove sulfur from sulfur-containing organic compounds by oxidative cleavage of C-S bond.

For another example, the Chinese patent with application number CN 01115920.0 discloses a method for controlling the process of microbial degradation of crude oil, including determining the type, concentration, dosage and other parameters of surfactant by studying the effect of surfactant on microbial growth and crude oil degradation. The disclosure also provides a degradation agent for petroleum pollutants, including oil-producing bacteria and identified surfactant. CN 01115920.0 also provides a method for using microorganisms to degrade petroleum pollutants, including injecting an identified petroleum pollutant degradation agent into the polluted environment. CN 01115920.0 allows to control the process of microbial degradation of crude oil, and reduce or eliminate the oil pollution in the environment through sharing of the surfactant and degradation bacteria.

However, there is no report about use of *Brevibacillus Agri*. and its preparation, and its metabolic organism in enhancing oil recovery.

In view of the technical gap existing in the prior art, the present disclosure provides a *Brevibacillus agri*, its use and a method for preparing surfactant.

SUMMARY OF THE INVENTION

The present disclosure provides a *Brevibacillus agri*, its use and method for preparing surfactant.

The present disclosure provides the following technical schemes.

A *Brevibacillus agri* strain, wherein the accession number of the *Brevibacillus agri* strain is CGMCC No. 9983.

In one aspect, the present disclosure provides a *Brevibacillus agri* preparation, wherein the *Brevibacillus agri* preparation comprises the *Brevibacillus agri* strain with accession number CGMCC No. 9983, wherein the Brevibacillus agri strain is a liquid bacterial preparation.

In another aspect, the present disclosure provides a method for preparing biosurfactant, wherein the method comprises fermenting the *Brevibacillus agri* or the *Brevibacillus agri* preparation in a nutrient medium to produce a lipopeptide biosurfactant.

In one embodiment, the nutrient medium comprises: $MgSO_4$ 0.2 g/L, $K_2HPO_4$ 1.0 g/L, $KH_2PO_4$ 1.0 g/L, $Na_2HPO_4$ 4.0 g/L, NaCl 10.0 g/L, $NaNO3$ 10.0 g/L, crude oil 10.0 g/L and molasses 2-3 g/L, pH is 7.0, and fermentation temperature is 25-60° C.

In one embodiment, the nutrient medium comprises 1-5 mL of solution of trace elements and 1-10 mL of solution of vitamin complex.

In one embodiment, the method further comprises removing bacteria after fermentation.

In one embodiment, the method for fermenting the *Brevibacillus agri* or the *Brevibacillus agri* preparation in a nutrient medium comprises the following steps:

1.1 inoculating the *Brevibacillus agri* strain preserved on slant culture medium on the culture plate through streak inoculation by inoculating loop, culturing at 30° C. for 20 h to activating;

1.2 inoculating the *Brevibacillus agri* strain from the culture plate into the primary seed shaker by picking three loops of bacteria, and culturing at 30° C. and 180 r/min for 18 h;

1.3 inoculating the primary seed liquid into the second stage shaker according to 2% of the volume of the primary seed shaker and culturing under the same conditions as in step 1.2 for 18 h;

1.4 inoculating the second stage liquid into the fermentation shaker according to 2% of the volume of the second stage shaker and culturing under the same conditions until the spore rate reaches 100% to obtain fermentation broth.

In one embodiment, the method further comprises a method for extracting the biosurfactant, the method for extracting the biosurfactant comprises the following steps:

2.1 adjusting the pH of the fermentation broth to 8, removing the bacteria by centrifuging twice at 4° C.

and 9000 r/min for 20 min, adjusting the pH of supernatant to 2.0 with 12 mol/L hydrochloric acid, observing flocculent precipitates, allowing the supernatant to stand at 4° C. overnight;

2.2 centrifuging the fermentation broth at 4° C. and 9000 r/min for 30 min, pouring supernatant out, washing the precipitate in the centrifuge tube with hydrochloric acid solution with pH of 2.0, adjusting the pH of precipitate to 7.0 with 1 mol/L NaOH, and freeze drying to obtain yellowish brown loose solid to prepare crude product of surfactant;

2.3 packing the crude product of surfactant with an aluminum foil, putting into a Soxhlet extractor, extracting the crude product of surfactant with 150 mL dichloromethane for 10 h, controlling the dripping rate of organic solvent at 1-2 drops per second, removing the solvent by rotary evaporation after extraction, washing the alkanes out with 3 times volume of n-hexane to obtain brownish yellow precipitate, and freeze drying to prepare the purified biosurfactant.

In yet another aspect, the present disclosure provides a biosurfactant.

In yet still another aspect, the present disclosure provides a method for preparing lipopeptide biosurfactant, wherein the lipopeptide biosurfactant is metabolized by the *Brevibacillus agri* strain.

In yet still another aspect, the present disclosure provides a use of the *Brevibacillus agri* strain in enhancing oil recovery.

In yet still another aspect, the present disclosure provides a use of the *Brevibacillus agri* preparation in enhancing oil recovery.

In yet still another aspect, the present disclosure provides a use of the biosurfactant in enhancing oil recovery.

Compared with the prior art, the present disclosure has the following beneficial effects:

1. The lipopeptide biosurfactant of the present disclosure has good physical properties, may effectively reduce the surface tension, and has good emulsification for petroleum, various hydrocarbons and lipids;
2. The *Brevibacillus agri* and its preparation may effectively enhance the crude oil recovery.

Depository information

Depository address: Institute of Microbiology, Chinese Academy of Sciences, No.3, No.1 courtyard, Beichen West Road, Chaoyang District, Beijing, China;

Depository date: Nov. 18, 2014;

Depository name: *Brevibacillus Agri*;

Depository institution: China General Microbiological Culture Collection Center(CGMCC);

Accession number: CGMCC No. 9983.

DETAILED DESCRIPTION OF THE EMBODIMENTS

Figure 1:
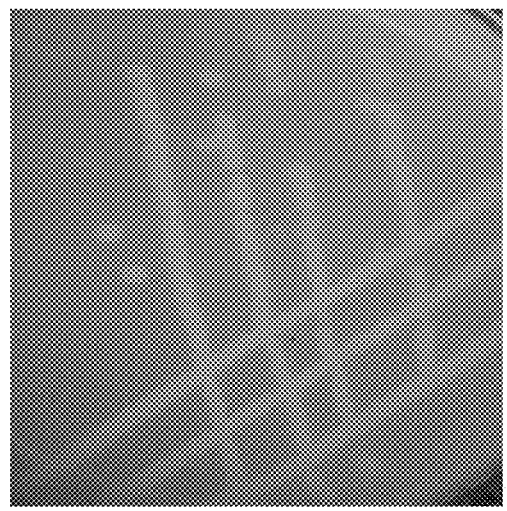
FIG. 1 shows the schematic diagram of the colony of B5-2 strain in Example 1 of the present disclosure.

The present disclosure is further described in combination with specific examples, and the characteristics and technical effects in application of *Brevibacillus Agri* of the present disclosure are described. The following examples are not intended to limit the present disclosure, but only to illustrate the present disclosure. Unless otherwise specified, the experimental methods used in the following examples will usually follow conventional conditions unless specific conditions are specified in the examples. Unless otherwise specified, the materials and reagents used in the following examples can be obtained from commercial sources.

The present disclosure provides a *Brevibacillus Agri* strain isolated from the extreme environment of oil reservoir. The strain has good characteristics of degrading crude oil. The Brevibacillus Agri strain and its preparation may degrade macromolecular hydrocarbons and polar compounds of crude oil, change the hydrophilic and lipophilic properties of water interfacial active substances of crude oil, reduce viscosity and enhance crude oil recovery. The present disclosure provides for the first time a method for preparing lipopeptide biosurfactant by fermentation of *Brevibacillus Agri* and a method for extracting metabolites of *Brevibacillus Agri*. The present disclosure also provides a *Brevibacillus agri* preparation and its use in enhancing oil recovery.

Example 1: Isolation, Identification and Deposition of Biosurfactant-Producing Strains 1. Enrichment Culture and Isolation of Biosurfactant-Producing Strains According to the conventional screening method, 10 mL of oil-water sample collected from oilfields of western China was put into 100 mL of sterilized crude oil culture medium (2% crude oil, V: V) and cultured at 30° C. and 180 rpm for 96 h. Then 5% of the enrichment culture solution of the experimental group with high emulsification and dispersion degree of crude oil was transferred to fresh culture medium and cultured at 30° C. and 180 rpm for 96 h. After repeated enrichment and cultivation for 10 rounds, the experimental group with the best emulsification and dispersion of crude oil was selected. 100 μL fermentation broth was spread on LB-agar-medium and cultured at 30° C. for 48 h; single colonies with different morphology were cultured on LB-agar-medium and purified by a streak plate method and cultured at 30° C. for 48 h. After enrichment culture, single colony was inoculated into the crude oil inorganic salt culture medium with crude oil as carbon source, and cultured at 30° C. and 180 rpm for 96 h. The degree of emulsification and dispersion of crude oil and the surface tension of fermentation broth were observed, the surface tension of the fermentation liquide was measured and the strain with the largest decrease in surface tension was selected.

In this example, through preliminary screening, it is found that there are microorganisms that can emulsify and disperse the crude oil well and reduce the surface tension of the culture medium in the sample. After the cultivation and domestication, a biosurfactant-producing strain is isolated and named. The diameter of oil drainage circle is 6.65 cm, and the surface tension of fermentation broth is reduced to 30.68 mn/m. The metabolites of B5-2 strain have excellent surface activity and can be used in microorganisms to enhance crude oil recovery.

TABLE 1

Determination of surfactant-producing microorganisms

| Strains | Optimum temperature/° C. | Surface tension mN/m | Diameter of oil drainage circle/cm |
|---------|--------------------------|----------------------|------------------------------------|
| B5-2    | 30                       | 30.68                | 6.65                               |

2. The physiological and biochemical identification and preservation of B5-2 strain are based on the "Manual Of Identification In Common Bacterial". The B5-2 strain is identified from the aspects of individual morphological characteristics, colony characteristics, staining reaction, physiological and biochemical reaction, and the genus name of B5-2 strain is identified. The identification includes morphological observation, Gram staining, catalase reaction, oxidase test, glucose oxidation fermentation test, methyl red test, etc. The results are shown in Table 2.

TABLE 2 identification results of physiological and biochemical characteristics of B5-2 strain

| Physiological and biochemical characteristics | | L1 strain |
|---|---|---|
| Unique carbon source test | Glucose | + |
| | Maltose | + |
| | Lactose | − |
| | Galactose | − |
| | Rhamnose | − |
| | Raffinose | − |
| | Sorbitol | − |
| | Sucrose | + |
| | Ammonium chloride | + |
| Unique nitrogen source test | Sodium nitrate | + |
| | Sodium nitrite | + |
| Indole test | | + |
| Hydrogen sulfide production test | | − |
| Methyl red test | | − |

TABLE 2-continued identification results of physiological and biochemical characteristics of B5-2 strain

| Physiological and biochemical characteristics | L1 strain |
|---|---|
| Acetylmethylcarbinol test | + |
| Starch hydrolysis test | + |
| Citrate utilization test | + |
| Temperature range for growth | 25° C.-60° C. |
| Salinity range for growth | >7% |

Figure 2:
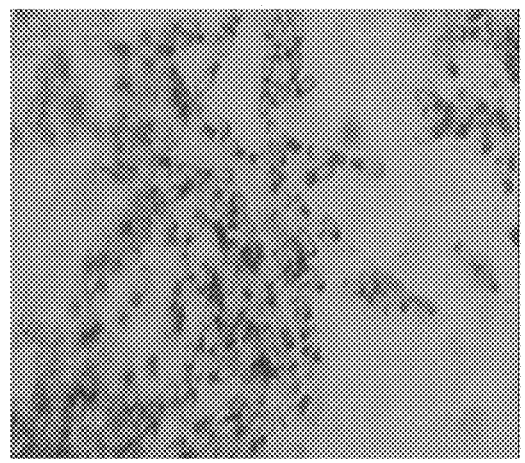
FIG. 2 shows the schematic diagram of Gram staining microscope observation of B5-2 strain in Example 1 of the disclosure.
Figure 3:
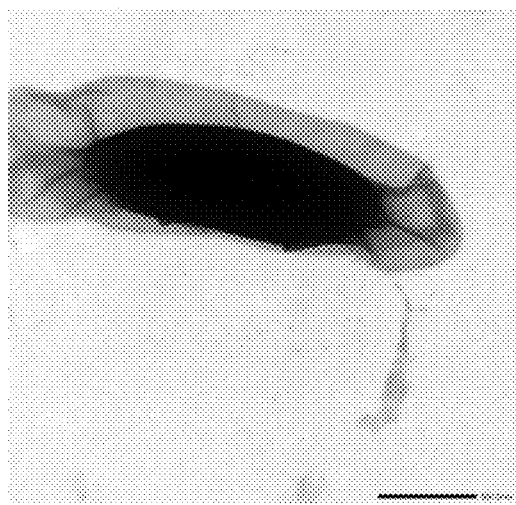
FIG. 3 shows the transmission electron microscope of B5-2 strain in Example 1 of the present disclosure.

The colony is round, having convex surface, milky white, smooth and moist surface. B5-2 strain is rod-shaped and produces spores, and the spores has expanded terminal. The micrograph is shown in FIG. 1 and FIG. 2. The electron micrograph of B5-2 strain made in the Institute of microbiology, Chinese Academy of Sciences is shown in FIG. 3. The electron micrograph of JEM-1400 shows that the B5-2 strain has capsule and surrounded periflagella.

According to the conventional strain identification method, the genomic DNA of B5-2 strain was extracted, and primers were designed for PCR amplification. The amplified products were detected by agarose gel electrophoresis, and DNA sequencing was performed by Sangon. It was determined that the B5-2 strain is Brevibacillus Agri. strain (the similarity was 99%) through the search and homology comparison of the PCR product sequence of B 5-2 in NCBI BLAST.

The B5-2 strain of this example can be preserved by using the following method:

(1) Short term preservation: the above-mentioned strains are inoculated on slant culture medium through streak inoculation, cultured at 35° C. for 48 h, and stored at 4° C.

(2) Long term preservation: a glycerol cryopreservation method may be used. The strains are inoculated from the fresh slant culture medium into the tube with 1.5 mL 30% sterilized glycerin by inoculating loop for cryopreservation at −80° C. Alternatively, a skimmed milk cryopreservation method may be used. The strains are inoculated from the fresh slant culture medium into the tube with sterilized skimmed milk for cryopreservation at −80° C.

*Brevibacillus Agri* B5-2 strain was deposited in China General Microbiological Culture Collection Center (Institute of Microbiology, Chinese Academy of Sciences, No.3, No.1 courtyard, Beichen West Road, Chaoyang District, Beijing, China;) on Nov. 18, 2014, with the accession number of CGMCC No. 9983.

Example 2: Extraction of B5-2 Strain Metabolites

1. Fermentation of B5-2 Strain

The fermentation culture medium of *Brevibacillus Agri* B5-2 strain included: $MgSO_4$ 0.2g/L, $K_2HPO_4$ 1.0 g/L, $KH_2PO_4$ 1.0 g/L, $Na_2HPO4$ 4.0 g/L, NaCl 10.0 g/L, $NaNO_3$ 10.0 g/L, crude oil (heavy oil) 10.0 g/L and molasses 2-3 g/L, pH 7.0; appropriate amount of solution of trace elements and vitamins complex, pH 6-8. The culture medium was sterilized at 115° C. for 30 min. The fermentation temperature was 30° C.

The strain preserved on slant culture medium on the culture plate was inoculated through streak inoculation with a inoculating loop, activated and cultured at 30° C. for 20 h. Then three loops of the strain was picked from the culture plate into the primary seed shaker (250 mL triangular flask, loading volume of liquid was 50 mL), and cultured at 30° C. and 180 r/min for 18 h (each inoculation loop contained more than 3 single colonies with obvious characteristics). The primary seed liquid was inoculated into the second stage shaker (250 mL triangular flask, the loading volume of liquid is 100 mL) in 2% of the volume of the primary seed shaker and cultured under the same conditions as in step 1.2 for 18 h. The second stage liquid was inoculated into the fermentation shaker (500 mL triangular flask, the volume of liquid is 150 mL) in 2% of the volume of the second stage shaker and cultured under the same conditions until the spore rate reaches 100% to obtain fermentation broth.

2. Extraction and Identification of Lipopeptide Produced By B5-2

The pH of fermentation broth was adjusted to 8, and the bacteria was removed by centrifuging twice at 4° C. and 9000 r/min for 20 min. The pH of supernatant was adjusted to 2.0 with 12 mol/L hydrochloric acid, flocculen precipitates were observed, and the supernatant was kept at 4° C. overnight; the fermentation broth was centrifuged at 4° C. and 9000 r/min for 30 min, the supernatant was poured out. The precipitate was washed in the centrifuge tube with hydrochloric acid solution with pH of 2.0. The pH of precipitate was adjusted to 7.0 with 1 mol/L NaOH, and freeze dried to obtain a yellowish brown loose solid to prepare crude product of surfactant. The crude product of surfactant was packed with an aluminum foil, and put into Soxhlet extractor. The crude product of surfactant was extracted with 150 mL dichloromethane for 10 h. The dripping rate of organic solvent was controlled at 1-2 drops per second. The solvent was removed by rotary evaporation after extraction. The alkanes were washed off with 3 folds of volume of n-hexane to obtain brownish yellow precipitate, and freeze dried to prepare the purified biosurfactant.

The brown precipitate obtained by acid precipitation method is identified as *Brevibacillus agri*. Generally, the surfactant produced by *Brevibacillus agri* is mainly the lipopeptide, which is a kind of charged biosurfactant. Therefore the extraction effect is better when using the equal-charge acid precipitation method.

3. Qualitative Analysis By Thin Layer Chromatography (TLC)

The thin-layer plate used in the experiment was silica gel plate, i.e. the adsorbent was silica gel. Therefore the results of thin-layer chromatography were mainly affected by the developing solvent.

(1) Preparation of developing solvent: the developing solvent was chloroform/methanol/water (65/15/2, V/V/V).

(2) It is better to first saturate the space of the chromatography chamber with the vapor of the developing agent. In order to accelerate the saturation process, the filter paper with developer solvent can be suspended in the chamber.

(3) The spotted thin layer plate was immersed into the developing solvent with a depth of 0.5-1.0 cm.

(4) When the frontier of the developing solvent moved to about 0.5-1.0 cm from the upper edge of the thin layer plate, the development of the developing solvent was stopped. The thin layer plate was quickly taken out and placed flat, and position of the frontier of the solvent was marked with a pencil.

(5) Visualization: the visualization reagent was put into the sprayer, and the visualization reagent was uniformly sprayed on the thin layer by washing ear ball, and then baked in the oven at 110° C. for 10 min.

TLC analysis and staining results showed that staining with ninhydrin directly failed to visualize. The thin layer plate was put into a sealed flask containing concentrated hydrochloric acid, hydrolyzed in situ at 150° C., and then stained with ninhydrin. Red spots were observed, indicating that there was no free amino acids, and free amino acids could be produced after acid hydrolysis, indicating that the substance itself did not contain free amino acids, which proved that it was a lipopeptide surfactant.

Example 3: Optimization of Lipopeptide-Producing Culture System of B5-2 Strain

The culture medium included seed culture medium, fermentation culture medium and slant culture medium Seed culture medium (g/L): $MgSO_4$ 0.2, $K_2HPO_4$ 1.0, $KH_2PO_4$ 1.0, $NH_4NO_3$ 1.0, yeast extract paste 1.0, $CaCl_2 \cdot 2H_2O$ 0.02, $FeCl_3$ 0.05, distilled water 1000 mL, pH 7.2;

Culture medium (g/L): $MgSO_4$ 0.2, $K_2HPO_4$ 1.0, $KH_2PO_4$ 1.0, $Na_2HPO_4$ 4.0, NaCl 10.0, peptone 10.0, crude oil 20.0, molasses 10.0, distilled water 1000 mL, pH 7.0;

Slant culture medium (g/L): beef extract 5.0, peptone 10.0, NaCl 5.0, agar 20.0, distilled water 1000 mL, pH 7.0.

1. Optimization of Carbon Source

Nutrients that can be used as carbon source in microbial cell structure or metabolites are all called carbon source. There are a wide range of carbon sources that can be used as microbial nutrients, ranging from simple inorganic substances ($CO_2$, carbonate) to complex organic carbon compounds (sugars, sugar derivatives, lipids, alcohols, organic acids, hydrocarbons, aromatic compounds, etc.). However, different microorganisms have different ability to utilize carbon sources. Some can widely use different types of carbon sources. For example, some species of *Pseudomonas* can use more than 90 kinds of carbon sources. However, the range of carbon sources that some microorganisms can use is very narrow. For example, *Methylosinus trichosporium* can only utilize methane and methanol; some cellulose decomposing bacteria can only use cellulose.

Screening an appropriate carbon source is one of the most important steps in the microbial enhanced oil recovery (MEOR). Considering oilfield applications and cost requirements, the mixture of heavy wax oil, vegetable oil, crude oil, liquid paraffin, crude oil and molasses is usually used as carbon source.

Figure 4:
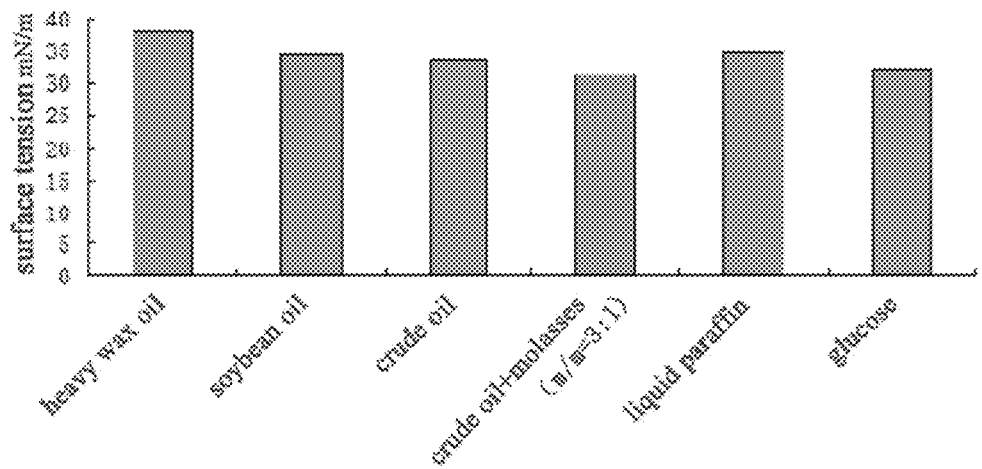
FIG. 4 shows the schematic diagram of the effect of different carbon sources on the surface tension in Example 3 of the present disclosure.

Based on the quality of carbon source, the dosage of carbon source is 2%, the inoculation amount of B5-2 strain is 5%, the culture temperature is 25° C., the culture time duration is 4 days, and the shaking speed of shaker is 180 r/min. The result of screening is shown in FIG. 4. Through the screening of different carbon sources, the result shows that the more suitable carbon source for lipopeptide production of B5-2 strain is the mixture of crude oil and molasses. Crude oil and molasses can promote the production of lipopeptide biosurfactant better than other carbon sources.

2. Optimization of Nitrogen Source

Nutrients that constitute the source of nitrogen in microbial cell substances or metabolites are all called nitrogen source. Its content in the dry matter of cells is second only to carbon and oxygen. Nitrogen is an important element of nucleic acid and protein. Therefore, it plays an important role in the growth and development of microorganisms. Nitrogen can be used by different microorganisms, regardless of molecular nitrogen or complex nitrogen compounds. However, different types of microorganisms can use different nitrogen sources. Nitrogen is an important component, which is the main elements of living substances such as protein and nucleic acid. Nitrogen accounts for 12%-15% of the dry weight of cells. Therefore, similar to carbon source, nitrogen sources are also the main nutrient of microorganisms. Yeast extract paste, peptone, $(NH_4)_2HPO_4$, sodium nitrate and urea are usually used as nitrogen sources for screening.

Yeast extract paste, peptone, $(NH_4)_2HPO_4$, sodium nitrate, urea and ammonium sulfate were used as nitrogen sources. the amount of nitrogen sources was 1%. The amount of carbon source crude oil and molasses mixture was 2%. the inoculation amount of B5-2 strain in seed liquid was 5%. The culture temperature was 25° C. The culture time duration was 4 days, and the shaking speed was 180 r/min.

Figure 5:
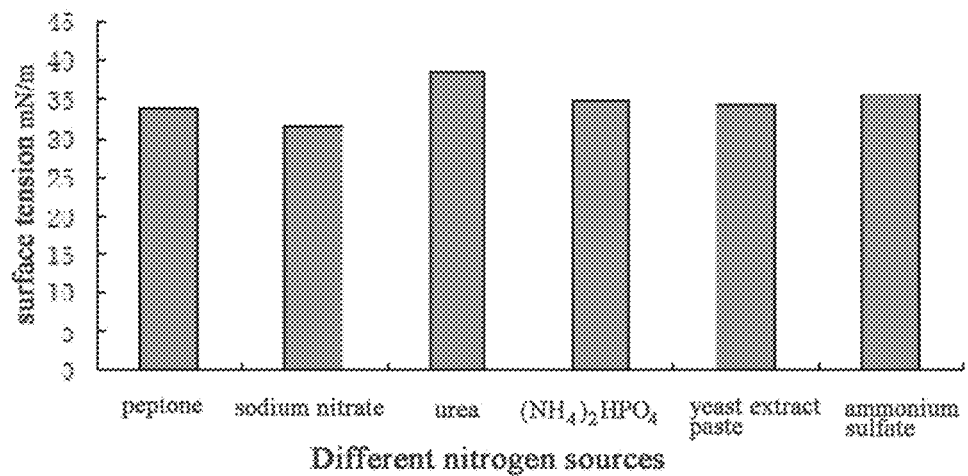
FIG. 5 shows the schematic diagram of the effect of different nitrogen sources on the surface tension in Example 3 of the present disclosure.

Nitrogen source is the basic nutrient source for the synthesis of cell substances, and its type and concentration determine the growth of bacteria, which affects the production of lipopeptide biosurfactant. After screening, it is found that, as shown in FIG. 5, in the aspect of lipopeptide production, inorganic nitrogen is better than organic nitrogen, and sodium nitrate is the best inorganic nitrogen.

3. Optimization of Culture Medium By Orthogonal Experiment

Single factor experiment was used to optimize the carbon source, nitrogen source and mineralization of fermentation culture medium, as well as the seed age, inoculation amount, temperature, oxygen demand and pH in the culture process. In addition, other components in the culture medium were also optimized and adjusted. $L_{16}$ ($4^5$) orthogonal experiment was used to reduce the number of experiments, as shown in Table 3 and Table 4.

TABLE 3

Factors and levels of orthogonal experiment

| | Factors | | | |
|---|---|---|---|---|
| Levels | Crude oil + molasses g/L | Sodium nitrate g/L | Sodium chloride g/L | Culture temperature ° C. |
| 1 | 3 | 5 | 5 | 25 |
| 2 | 6 | 10 | 10 | 29 |
| 3 | 9 | 15 | 15 | 33 |
| 4 | 12 | 20 | 20 | 37 |

TABLE 4

Results of $L_{16}$ ($4^5$) orthogonal experiment

| Number | A crude oil + molasses g/L | B Sodium nitrate g/L | C Sodium chloride g/L | D Culture temperature ° C. | E surface tension m $Nm^{-1}$ |
|---|---|---|---|---|---|
| 1 | 3 | 5 | 5 | 25 | 36.85 |
| 2 | 3 | 10 | 10 | 29 | 34.94 |
| 3 | 3 | 15 | 15 | 33 | 37.54 |
| 4 | 3 | 20 | 20 | 37 | 40.42 |
| 5 | 6 | 5 | 10 | 33 | 38.47 |
| 6 | 6 | 10 | 5 | 37 | 39.41 |
| 7 | 6 | 15 | 20 | 25 | 30.83 |
| 8 | 6 | 20 | 15 | 29 | 31.42 |
| 9 | 9 | 5 | 15 | 37 | 41.52 |
| 10 | 9 | 10 | 20 | 33 | 36.88 |
| 11 | 9 | 15 | 5 | 29 | 35.48 |
| 12 | 9 | 20 | 10 | 25 | 29.45 |
| 13 | 12 | 5 | 20 | 29 | 34.58 |
| 14 | 12 | 10 | 15 | 25 | 31.29 |
| 15 | 12 | 15 | 10 | 37 | 37.53 |
| 16 | 12 | 20 | 5 | 33 | 33.51 |

TABLE 4-continued

Results of $L_{16}$ ($4^5$) orthogonal experiment

| Number | A crude oil + molasses g/L | B Sodium nitrate g/L | C Sodium chloride g/L | D Culture temperature ° C. | E surface tension m $Nm^{-1}$ |
|---|---|---|---|---|---|
| Mean 1 | 37.438 | 37.855 | 36.312 | 32.105 | |
| Mean 2 | 35.032 | 35.630 | 35.097 | 34.105 | |
| Mean 3 | 35.832 | 35.345 | 35.443 | 36.600 | |
| Mean 4 | 34.227 | 33.700 | 35.677 | 39.720 | |
| Range | 3.211 | 4.155 | 1.215 | 7.615 | |

The intuitive analysis method is used for the results of the orthogonal experiment. The results of the intuitive analysis are shown in Table 3 and Table 4. From the calculation results in Table 4, FIG. 4 and FIG. 5, it can be seen that $A_4B_4C_2D_1$ is the optimal combination. i.e. the concentration of carbon source is 12.0 g/L, the concentration of sodium nitrate is 20.0 g/L, the concentration of sodium chloride is 10.0 g/L, and the culture temperature is 25° C., the gradient analysis result is $R_D > R_B > R_A > R_C$. i.e. the culture temperature has the greatest influence on the lipopeptide production.

Example 4: The Effect On Crude Oil (Heavy Oil)

1. Emulsifying Property

Emulsification was a phenomenon in which water or organic solvents are dispersed in the organic or aqueous phase in the form of tiny droplets. i.e. when a liquid phase is dispersed in droplets in another continuous liquid phase, an emulsion is formed. 5 mL of liquid paraffin and 5 mL of surfactant solution were added into a test tube, and the test tube was oscillated with a vortex oscillator for 1 min and then kept still. The volume of the aqueous phase, emulsified phase and oil phase were measured at different times. The emulsifying capacity is expressed by the ratio of the volume of emulsified phase to the total volume.

Figure 6:
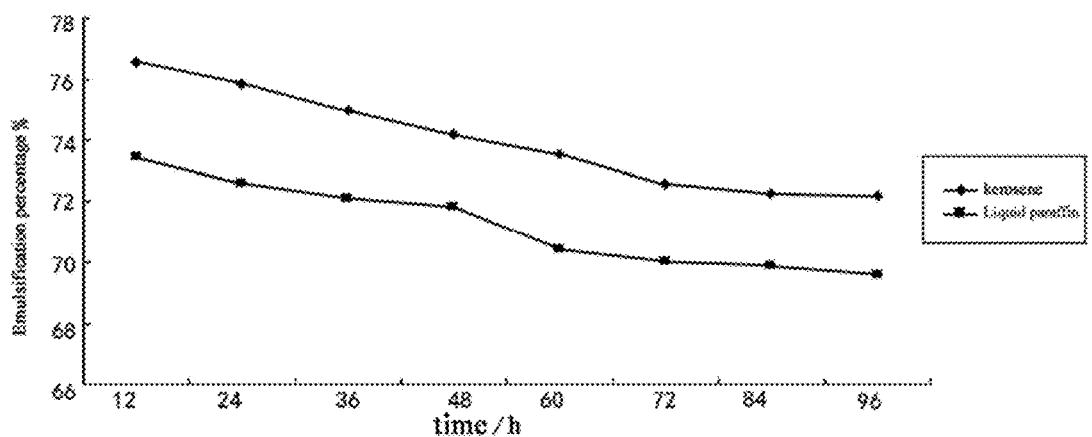
FIG. 6 shows the schematic diagram of emulsifying property test of surfactant produced by B5-2 strain in Example 4 of the disclosure.

The results of the emulsification stability of lipopeptide biosurfactant produced by B5-2 strain to kerosene and liquid paraffin are shown in FIG. 6. It can be seen from FIG. 6 that lipopeptide biosurfactant has good emulsifying capacity. After 96 hours, the emulsifying capacity of lipopeptide biosurfactant produced by B5-2 strain on kerosene oil and water can still be maintained above 72%, so it is a good emulsifier. This is because the biosurfactant is a lipopeptide mixture containing multiple components, with diverse structures and strong affinity to the oil/water interface, which stabilizes the emulsified phase, which proves that the lipopeptide has a good application prospect.

2. Results of Oil Spreading Activity

Water was added to a culture disk, and 200 μL n-dodecane was dripped in the culture disk. After the oil film was formed, 10 μL fermentation liquid was dripped into the center of the oil film. The diameter and stability of the clear zone was observed. Experiment for three parallel samples was conducted to give a deviation within 5%, and the average value was taken as the clear zone diameter of the sample.

The lipopeptide biosurfactant produced by B5-2 strain has a diameter of 6.6 cm for n-dodecane, indicating that it has good oil drainage performance.

3. Results of Test For Electricity Charging of Biosurfactant (1) Methylene blue-chloroform method was used to determined anionic surfactant.

5 mL sample was added into 25 mL test tube, then 10 mL methylene blue solution and 5 mL chloroform were added. The test tube was shaken for several minutes. If the solution contains anionic surfactants, then the chloroform layer turns blue.

(2) Bromophenol blue method was used to determined cationic surfactant.

The pH of the sample solution was adjusted to 7.0, 5 mL of the sample solution was added into the 25 mL test tube, and then 2-5 drops of the prepared bromophenol blue solution were added into the test tube. If the solution turns dark blue, it contains cationic surfactants.

The results of the determination method of anionic surfactant (Methylene blue-chloroform method) and cationic surfactant (bromophenol blue method) showed that the chloroform layer turned blue, indicating that the biosurfactant in the sample was an anionic surfactant.

4. Changes of Surface Tension, PH and Viscosity Before and After the Action of B5-2 Strain Surface tension is an important parameter of liquid, which is usually used to reflect the surface properties of liquid, i.e. the amount of surfactants in liquid. The lower the surface tension is, the higher the content of surfactants in the liquid. In the process of microbial enhanced oil recovery, some microbial metabolites contain certain surfactants, which are generally called biosurfactant. Biosurfactant can reduce the interfacial tension of water/oil/rock, emulsify crude oil, and change the surface wettability of reservoir pores. However, it is difficult to directly measure the content of biosurfactant in microbial fluid. The surface tension is often used to evaluate the activity of the microbial liquid. Microbial metabolites such as acid and surfactant production are the important mechanism of microbial enhanced oil recovery. The ability of reducing surface tension and pH change are the basic indexes to evaluate the performance of bacteria. The ability of producing surfactant can reduce the interfacial tension of oil and water, and reduce the capillary force of enhanced oil, so as to improve oil recovery. The ability of microorganism to reduce the oil-water interface can be used to determine the ability of the strains to produce active agents.

(1) Study On Surface Tension and PH 200 mL fermentation culture medium was put into 500 mL triangular flask and cultured on a rotary shaker (180 r/min) at the actual temperature of the oilfield for 4 days. The fermentation broth was centrifuged to remove the bacteria, and then the supernatant was filtered with filter paper to remove the residual oil in the supernatant as much as possible.

The surface tension was measured by DCA322 contact angle analyzer from CAHN company of US. The hanging plate method was used to measure the surface tension of microbial liquid. The whole measuring process of the instrument was automatically completed under the control of a computer program.

In the test, the nutrition solution was prepared by using distilled water and Distilled water was used as the reference sample. The determined surface tension of blank culture medium was 64.38 mN/m.

B5-2 strain solution was cultured under different temperature and mineralization degree for 4 days, and then oil and water were separated. The pH and surface tension of bacteria solution were measured. The experimental data was shown in Table 5. The results show that:

1) B5-2 strain reduces the surface tension of oil samples from three oil wells in a western oilfield, but the reduction degree of the surface tension of different crude oils by B5-2 strain is different. The surface tension of TH191 crude oil, TH291 crude oil and TH222 crude oil are decreased by 50.26%, 45.46% and 47.91%, respectively.

2) The pH decreased from 7.2 to acid, indicating that acid is produced in the degradation process.

TABLE 5

Changes of surface tension and pH of crude oil treated by B5-2 strain

| Sample | Temperature | Surface tension | Reduction rate (%) | pH |
| --- | --- | --- | --- | --- |
| TH191 | 25° C. | 32.02 | 50.26 | 6.5 |
| TH291 | 25° C. | 35.11 | 45.46 | 6.6 |
| TH222 | 25° C. | 33.53 | 47.91 | 6.3 |

(2) Change of Crude Oil Viscosity

In oil recovery engineering, crude oil viscosity is a key factor affecting crude oil production. The lower the oil viscosity and the better the fluidity, the easier it is to be recovered out of the ground. Therefore, during the development of oil recovery technology, various methods of reducing the crude oil viscosity have been studied. Many previous research results show that some microorganisms can reduce the crude oil viscosity after interacting with crude oil. There are three reasons. First, the degradation of crude oil by microorganisms destroys the network structure formed by colloids and asphaltenes in crude oil as particles, i.e. it reduces the relative content of heavy components in crude oil and improves the fluidity of crude oil. Second, microorganisms produce some organic solvents in the process of reproduction and metabolism to dilute crude oil. The third reason may be that the surfactant produced by microbial metabolism has an emulsifying effect on crude oil to form oil-in-water emulsion, thus reducing the viscosity of crude oil. The ability of microorganisms to reduce the viscosity is also considered an important parameter when screening and evaluating microbial strains for oil recovery.

In the experiment, the viscosity was measured by BROOK FILELD II tumble fluidimeter imported from the US. 200 mL fermentation culture medium was filled in 500 mL triangular flask and cultured on a rotary shaker (180 r/min) at the actual temperature of the oilfield for 4 days. After 4 days, the bacteria solution was separated from the oil, centrifuged by a high-speed centrifuge at 9000 rpm for 10 minutes to dehydrate the oil. The dehydrated oil sample was poured into the fluidimeter. The temperature of the circulating water bath of the fluidimeter is set to 65° C., install U2 rotor on the fluidimeter. The viscosity of the oil sample was measured at the speed of 1.5 RPM after the sample temperature in the fluidimeter was stable. The viscosity reduction ability of bacteria solutions through the viscosity change before and after the action of oil and bacteria solution were compared.

$$\text{Viscosity reduction rate} = (\eta_{before} - \eta_{after})/\eta_{before} * 100\%$$

$\eta_{before}$ is the viscosity of crude oil before microbial action, and $\eta_{after}$ is the viscosity of crude oil after microbial action.

The results of crude oil viscosity reduction by indigenous bacteria B5-2 are shown in Table 6.

TABLE 6

Changes of crude oil viscosity after the action of B5-2 strain

| Sample | Before viscosity reduction (mPa · s) | After viscosity reduction (mPa · s) | viscosity reduction rate (%) |
|---|---|---|---|
| TH191 | 46.9 | 31.3 | 33.3 |
| TH291 | 51.3 | 36.5 | 28.8 |
| TH222 | 52.2 | 35.2 | 32.6 |

The results of viscosity reduction experiment in Table 6 show that the B5-2 strain has good viscosity reduction effect on the three kinds of crude oil. The viscosity reduction rates of B5-2 on TH191 crude oil, TH291 crude oil and TH222 crude oil are 33.3%, 28.8% and 32.6%, respectively.

Example 5: Changes in Components of Crude Oil Before and After Bacterial Degradation Of B5-2

1. Component Analysis of Crude Oil

Changes in the components before and after the action of the indigenous bacteria on the crude oil of Xinjiang Oilfield were evaluates indoor. The four components are saturated hydrocarbon, aromatic hydrocarbon, gum asphaltene and non-hydrocarbon.

Figure 7:
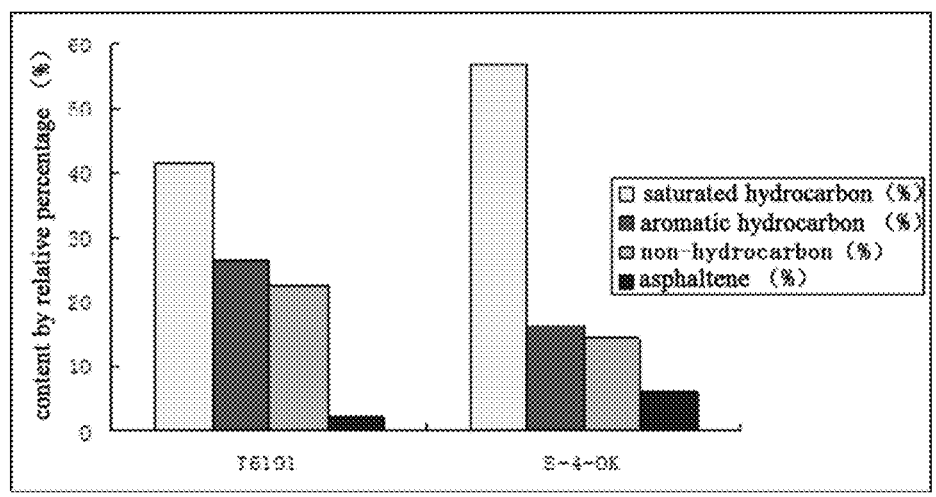
FIG. 7 shows the schematic diagram of changes in the mass fraction of crude oil components before and after the action of B5-2 strain in Example 5.

After 7 days of cultivation at 25° C. and 180 r/min in air shaker, the crude oil was degraded to a certain extent and emulsified. The crude oil was collected in the sample flask, centrifuged on the high-speed centrifuge (8000 r/min, centrifugation time is 1 min), and the water at the bottom of the sample flask was removed with 5 mL syringe. The sample flask was put in a refrigerator at 4° C. Then four component analysis and mass spectrometry analysis were performed. The content of each component of crude oil changes, as shown in Table 7 and FIG. 7.

TABLE 7

Relative content of crude oil components before and after the action of B5-2 strain

| Items | Saturated hydrocarbon (%) | Aromatic hydrocarbon (%) | Non-hydrocarbon (%) | Asphaltene (%) |
|---|---|---|---|---|
| Before degradation | 41.38 | 26.29 | 22.41 | 2.16 |
| After degradation S-4-OK | 56.85 | 16.33 | 14.29 | 6.12 |

The results of the B5-2 strain degradation test of crude oil in the western oilfield show that the relative content of saturated hydrocarbon, aromatic hydrocarbon, non-hydrocarbon and asphaltene has changed significantly. The relative content of saturated hydrocarbon and asphaltene increases, while the relative content of aromatic hydrocarbon and non-hydrocarbon decreases in varying degrees, which indicates that microorganisms preferentially degrade high carbon chain components, resulting in the increase of relative content of saturated hydrocarbon, and degradation of aromatic hydrocarbon and non-hydrocarbon components by B5-2 strain, and increasing the relative content of asphaltenes.

2. Results of Chromatography-Mass Spectrometry

Executive standard: GB/T 18606-2001 The Standard Test Method for Biomarker in Sediment and Crude Oil By GC-MS Instrumentation: Agilent 7890-5975c chromatography-mass spectrometer Test conditions: chromatography; carrier gas: 99.999% helium; injection port temperature: 300° C.; transmission line temperature: 300° C.; chromatographic column: HP-5MS elastic quartz capillary column (60 m×0.25 mm×0.25 m); column temperature: initial temperature: 50° C. for 1 min; 20° C./min to 120° C., 4° C./min to 250° C., then 3° C./min to 310° C., keep for 30 mins; carrier gas flow rate: 1 mL/min; mass spectrometry EI source, absolute voltage: 1047 V; full scan.

Figure 8:
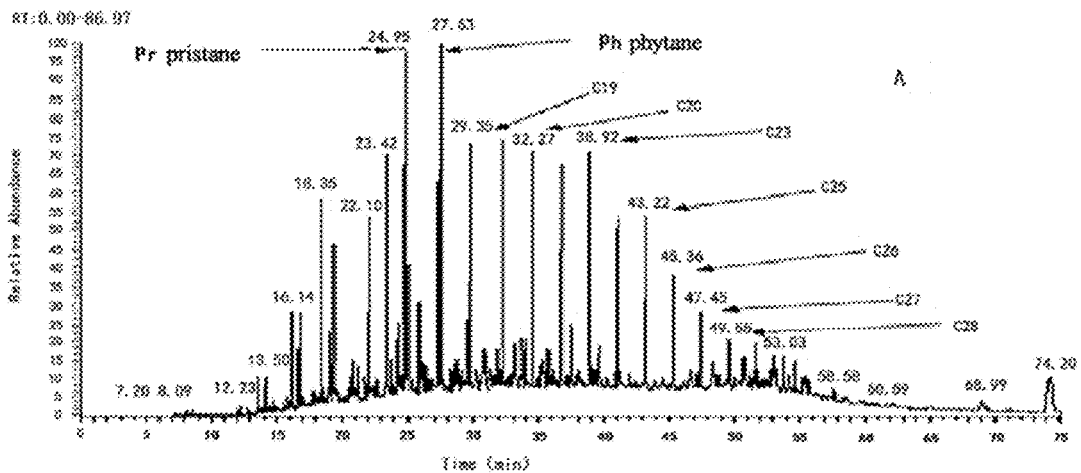
FIG. 8 shows the schematic diagram of the chromatographic-mass spectrometry(GC/MS) analysis of the content of saturated hydrocarbon components before the action of B5-2 strain in Example 5 of the present disclosure.
Figure 9:
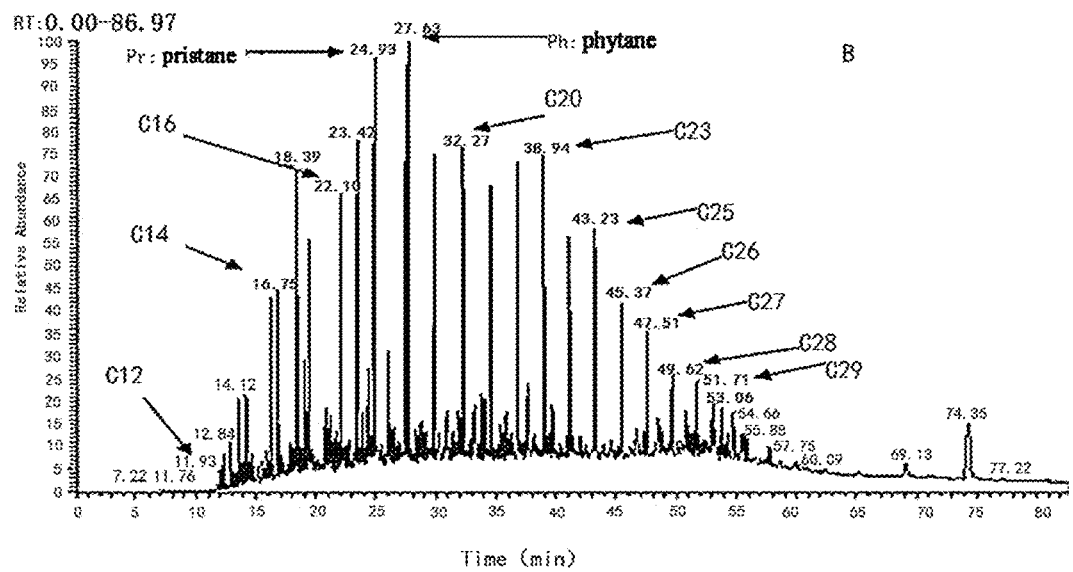
FIG. 9 shows the schematic diagram of the chromatography-mass spectrometry(GC/MS) analysis of the content of saturated hydrocarbon components after the action of B5-2 strain in Example 5 of the present disclosure.

As shown in FIG. 8 and FIG. 9, the ratio of pristane (Pr) and phytane (Ph), n-nonadecane and n-eicosane changes to a certain extent, the relative content of C27 and C28 decreases, and the proportion of alkanes with carbon number less than 16 increases after the action of B5-2 strain, indicating that the high carbon chain component is transformed into low carbon chain component by the indigenous bacteria, thus the light components increase. GC/MS analysis showed that B5-2 strain has not degrade low-carbon number saturated hydrocarbons significantly, and mainly degrades some high carbon alkanes.

Figure 10:
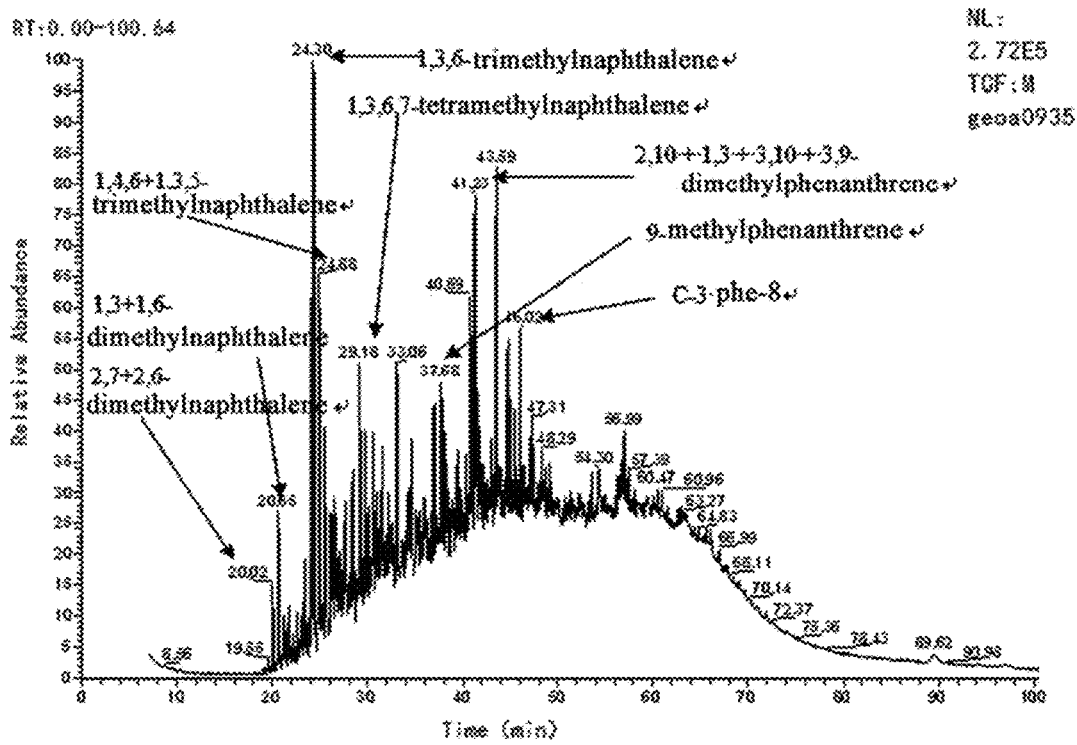
FIG. 10 shows the chromatography-mass spectrometry (GC/MS) spectrum of aromatic hydrocarbon of TH191 crude oil in Example 5 of the disclosure.
Figure 11:
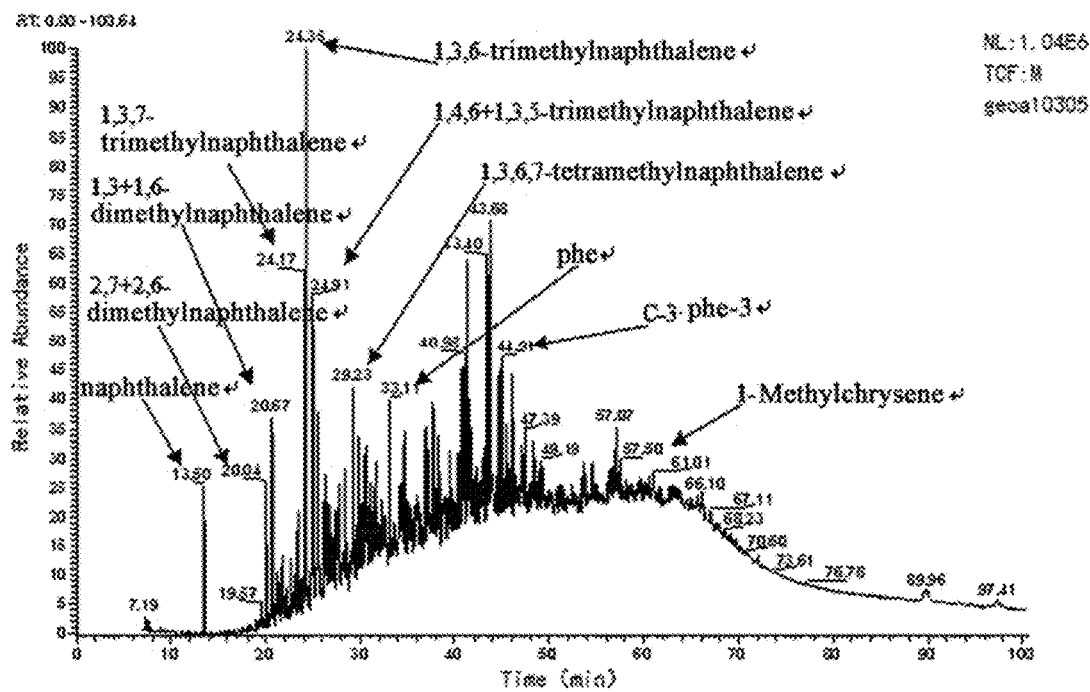
FIG. 11 shows the GC/MS spectrum of aromatic hydrocarbons after the action of B5-2 strain in TH191 crude oil in Example 5 of the disclosure.

As shown in FIG. 10 and FIG. 11, aromatic hydrocarbons are obviously degraded, especially the aromatic hydrocarbons below C20. Trimethylnaphthalenes are significantly degraded, phenanthrenes are significantly degraded, and the proportion of dimethylnaphthalene/trimethylnaphthalene and phenanthrene is significantly changed. GC/MS analysis results show that B5-2 strain preferentially degrade naphthalene and phenanthrene, and mainly degrade aromatic hydrocarbons below C20. The results show that B5-2 strain can effectively degrade the aromatic hydrocarbons below C20 and make the components of crude oil change obviously.

3. Changes of Polar Heteroatom Compounds

The composition changes of TH191 heavy oil before and after the action of B5-2 strain were analyzed by linear ion trap fourier-transform ion cyclotron resonance mass spectrometry (FT-ICR). After microbial degradation, the content of N compounds in crude oil decreased from about 70% to less than 20%, and the content of $O_2$ compounds decreased from more than 20% to less than 5%. The proportions of NO and $NO_2$ decreases in varying degrees. $NO_3$ and NS compounds may be decomposed by microorganisms, while the content of $O_3$ compounds increases significantly, with the proportion being more than 70%.

Figure 12:
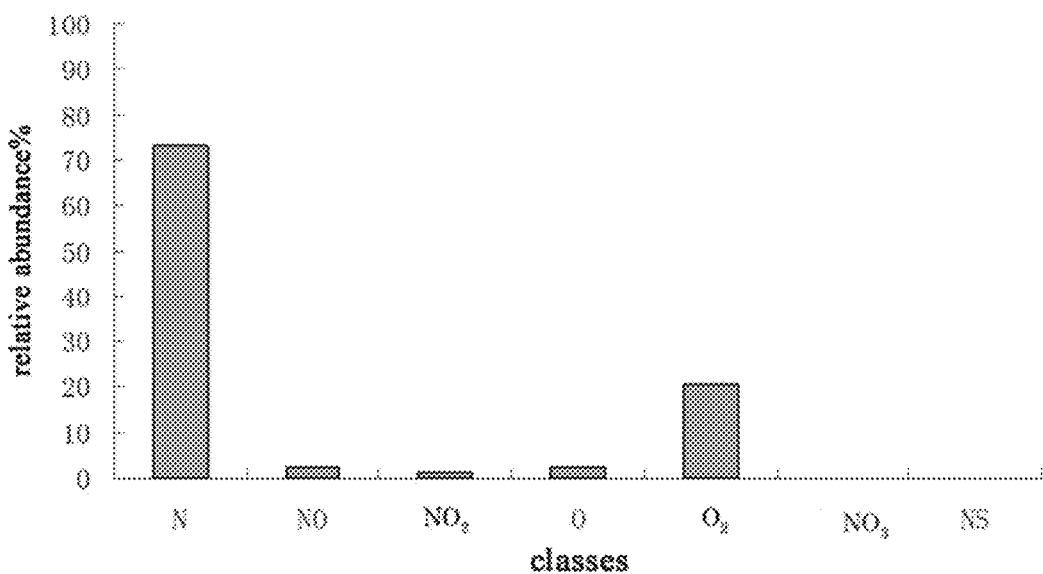
FIG. 12 shows the schematic diagram of the relative abundance of basic heteroatoms in crude oil TH191 before degradation in Example 5 of the present disclosure.
Figure 13:
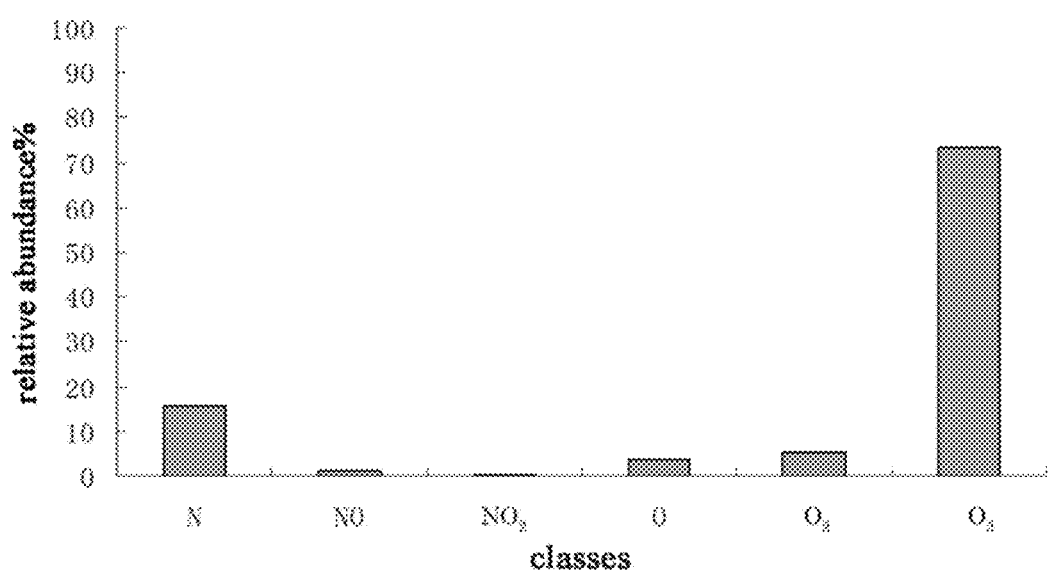
FIG. 13 shows the relative abundance of basic heteroatoms in crude oil TH191-S-4-OK after degradation in Example 5 of the present disclosure.

Relative abundance is defined as the intensity of each peak in the mass spectrum divided by the sum of the intensities of all identified peaks (except for isotopic peaks). Even if the relative abundance of a given class in two samples is the same, its absolute abundance is not necessarily the same, because it depends on the abundance of other classes. The relative abundances of crude oil TH191 and heteroatoms after the action of B5-2 strain are shown in FIG. 12 and FIG. 13. In FIG. 12, N compounds account for the majority of heteroatoms, more than 70%, and other types of heteroatoms accounted for a relatively low proportion: the content of $O_2$ is the second, more than 20%. The content of NO, $NO_2$, O are less than 5%, with trace amounts of $NO_3$ and NS. which can be ignored. As shown in FIG. 12, the content of N compounds after microbial degradation decreases significantly, less than 20%. The proportion of NO and $NO_2$ decreases. After microbial degradation, $NO_3$ and NS compounds are decomposes by microorganisms, which are not shown in FIG. 13. However, O₃ increases significantly, accounting for more than 70%, which may be due to the formation of a large amount of oxygen-containing acids. It shows that after the action of B5-2 strain, the neutral nitrogen heteroatom compounds of the polar compounds in the oil-water interface are degraded obviously. As a result, the formation of highly hydrophilic acidic compounds, resulting in the change of the hydrophobicity and lipophilicity of the interfacial substances on the crude oil, i.e. the lipophilicity of crude oil-water interfacial active substances is reduced. The hydrophilicity of crude oil is enhanced, which eventually lead to the reversing of the crude oil emulsion and forming the oil-in-water emulsion. In addition, the viscosity is greatly reduced, the fluidity and the oil recovery is enhanced.

Example 6: Simulation Test For Oil Displacement

. Preparation of Bacteria Solution For Oil Displacement 150 mL surfactant bacteria fermentation culture medium and 3 L inorganic salt culture medium were prepared. The medium was autoclaved at 121° C. for 20 min. B5-2 strain was activated and inoculated to the fermentation culture medium, and cultured at 25° C. and 180r/min for 24 h. The fermentation broth was added to 3L enhancing oil medium at 10%, and cultured at 25° C. and 180 r/min for 4 days. The fermentation broth was taken out and put into a 4° C. refrigerator.

2. Physical Simulation Test For Core Flooding

The process of oil displacement was connected, which process was composed of microinjection pump (gas cylinder for pressure source of constant pressure displacement), high pressure vessel, core model and oil-water separation metering tube. The above four parts were connected by pipelines and valves. The pressure gauge was installed as required to display the pressure values. The parts that need to maintain the experimental temperature were installed in the incubator.

Two artificial rock cores of TH121 and TH122 with gas permeability of 100-200md were selected to inject B5-2 strain bacteria solution 2PV, and shut in the well for 4 days, and the oil displacement effect was measured.

(1) Saturation Of Core With Water

The artificial core with gas permeability of about 200md was weighed the dry weight and then put into a wide mouth bottle. The wide mouth bottle was vacuumed with vacuum pump for three hours, and then the simulated formation water was added to make the core completely immersed in water. The vacuum pump was turned on until the vacuum gauge read zero, and then the artificial core was taken out, and the wet weight was weighed to get the of pore volume the core.

(2) Saturation Of Core With Oil

The core was put into a core holder, and the core holder was put into a 40° C. incubator. The dehydrated crude oil was added into a steel vessel. The pipeline was connected. The constant-flux pump was turned on to press the crude oil into the core. When 3-4 mL crude oil flowed out of the outlet end of the core holder, the saturated oil was over. The crude oil saturation was obtained based on the volume of the driven water.

(3) Water Flooding

The simulated formation water was put into the steel container. The pipeline for oil displacement was connected. The constant-flux pump was turned on for oil displacement. 5 mL test tube was used to receive the crude oil at the export of the core holder, and counting was made every 10 minutes until the water content reached 95%.

(4) Oil Displacement By Microorganism

The B5-2 strain bacteria solution was put into a steel container, the pipeline was connected for oil displacement. The amount of crude oil expelled was recorded. The constant-flux pump was closed after reaching the specified PV. The B5-2 strain bacteria solution was shut in the well at 50° C. for 4 days.

(5) Follow Up Water Flooding

After the specified well-shut time, follow-up water flooding was performed on the core, the amount of crude oil driven was recorded, and the value of the enhanced crude oil recovery factor was calculated.

The cores used for biosurfactant producing B5-2 strain were TH121 and TH122. The physical properties of two homogeneous artificial cores are shown in Table 8. When the two cores were water flooded to 95% of water content, the biosurfactant produced by B5-2 strain bacteria solution was injected, and shut in the well for 4 days. The subsequent water flooding was performed to obtain the recovery ratio. The results are shown in Table 8.

TABLE 8 physical properties of homogeneous cores

| | Diameter mm | Length mm | Pore volume mL | Porosity % | Permeability $10^{-3}$ μm² |
|---|---|---|---|---|---|
| Blank | 25 | 71.5 | 9.33 | 25.12 | 167.54 |
| TH121 | 25 | 70.3 | 8.79 | 25.23 | 161.32 |
| TH122 | 25 | 69.5 | 8.68 | 25.59 | 158.33 |

Table 8 shows the physical properties of TH121 and TH122. The physical parameters of the two cores are roughly the same. The gas permeability is about 160 md, the pore volume is about 25%, and the oil saturation is about 82%. According to the B5-2 strain enhancing oil experimental data, for TH121 and TH122 cores, the increase in oil recovery rate after the action of 120mg/L B5-2 strain bacterial solution is 10-12%, respectively. The enhancing oil effect of the B5-2 strain is obvious.

The present disclosure is not limited by the above-mentioned examples. The above-mentioned examples and the description only illustrate the principle of the present disclosure. On the premise of not departing from the spirit and scope of the present disclosure, there will be various changes and improvements. These changes and improvements fall into the scope of the present disclosure claimed. The scope of the present disclosure is defined by the attached claims.

What is claimed is:

1. A method for preparing biosurfactant, wherein the method comprises fermenting a *Brevibacillus agri* strain in a nutrient medium to produce a lipopeptide biosurfactant, wherein the *Brevibacillus agri* strain is *Brevibacillus agri* deposited with the China General Microbiological Culture Collection Center (CGMCC) with CGMCC deposit number 9983, wherein the nutrient medium comprises: $MgSO_4$ 0.2 g/L, $K_2HPO_4$ 1.0 g/L, $KH_2PO_4$ 1.0 g/L, $Na_2HPO_4$ 4.0 g/L, NaCl 10.0 g/L, $NaNO_3$ 10.0 g/L, crude oil 10.0 g/L and molasses 2-3 g/L, pH is 7.0, and a fermentation temperature is 25-60° C.

2. The method according to claim 1, wherein the nutrient medium further comprises 1-5 mL of a solution of trace elements and 1-10 mL of a solution of a vitamin complex.

3. The method according to claim 1, further comprising removing the *Brevibacillus agri* strain after fermentation.

4. The method according to claim 1, further comprising obtaining the lipopeptide biosurfactant.

5. The method according to claim 1, wherein the lipopeptide biosurfactant is a metabolite of the *Brevibacillus agri* strain.

6. The method according to claim 1, wherein the *Brevibacillus agri* strain is a liquid bacterial preparation.

7. The method according to claim 6, wherein the nutrient medium further comprises 1-5 mL of a solution of trace elements and 1-10 mL of a solution of a vitamin complex.

8. The method according to claim 6, further comprising removing the *Brevibacillus agri* strain after fermentation.

9. The method according to claim 4, wherein the nutrient medium further comprises 1-5 mL of a solution of trace elements and 1-10 mL of a solution of a vitamin complex.

10. The method according to claim 4, further comprising removing the *Brevibacillus agri* strain after fermentation.

\* \* \* \* \*